United States Patent
Kachlany et al.

(10) Patent No.: US 9,352,017 B2
(45) Date of Patent: May 31, 2016

(54) COMBINATION THERAPY WITH LEUKOTOXIN

(75) Inventors: Scott Kachlany, Bridgewater, NJ (US); Benjamin Belinka, Kendall Park, NJ (US)

(73) Assignees: RUTGERS, THE STATE UNIVERSITY OF NEW JERSEY, New Brunswick, NJ (US); ACTINOBAC BIOMED, INC., Kendall Park, NJ (US)

( * ) Notice: Subject to any disclaimer, the term of this patent is extended or adjusted under 35 U.S.C. 154(b) by 0 days.

(21) Appl. No.: 14/005,372

(22) PCT Filed: Mar. 16, 2012

(86) PCT No.: PCT/US2012/029476
§ 371 (c)(1), (2), (4) Date: Nov. 13, 2013

(87) PCT Pub. No.: WO2012/125942
PCT Pub. Date: Sep. 20, 2012

(65) Prior Publication Data
US 2014/0073578 A1  Mar. 13, 2014

Related U.S. Application Data

(60) Provisional application No. 61/453,162, filed on Mar. 16, 2011.

(51) Int. Cl.
| | |
|---|---|
| *A61K 38/00* | (2006.01) |
| *C07K 14/195* | (2006.01) |
| *A61K 38/16* | (2006.01) |
| *A61K 45/06* | (2006.01) |
| *A61K 31/136* | (2006.01) |
| *A61K 31/255* | (2006.01) |
| *A61K 31/506* | (2006.01) |
| *A61K 31/704* | (2006.01) |
| *A61K 31/7048* | (2006.01) |

(52) U.S. Cl.
CPC ............ *A61K 38/164* (2013.01); *A61K 31/136* (2013.01); *A61K 31/255* (2013.01); *A61K 31/506* (2013.01); *A61K 31/704* (2013.01); *A61K 31/7048* (2013.01); *A61K 45/06* (2013.01); *C07K 14/195* (2013.01)

(58) Field of Classification Search
None
See application file for complete search history.

(56) References Cited

U.S. PATENT DOCUMENTS

| | | | |
|---|---|---|---|
| 2009/0075883 A1* | 3/2009 | Kachlany | 514/12 |
| 2011/0039863 A1 | 2/2011 | Hilberg et al. | |
| 2011/0053893 A1 | 3/2011 | Wu et al. | |

OTHER PUBLICATIONS

Kachlany et al. 2010 (Anti-leukemia activity of a bacterial toxin with natural specificity for LFA-1 on white blood cells; Leukemia Res 34: 777-785).*
Topaly et al. 2002 (Rational for combination therapy of chronic myelogenous leukaemia with imatinib and irradiation or alkylating agents: implications for pre-transplant conditioning; British Journal of Cancer 86: 1487-1493).*
Kreitman et al. 2001 (Synergistic targeting of leukemia with leukotoxin and chemotherapy; Leukemia Research 35:1438-39).*
Gupta et al. 2001 (In vitro synergism between LFA-1 targeting leukotoxin (LeukotheraTM) and standard chemotherapeutic agents in leukemia cells; Leukemia Research 35:1498-1505).*
Kachlany, S.C, et al., "Secretion of RTX Leukotoxin by Actinobacillus Actinomycetemcomitans," Infect Immun, Nov. 2000, vol. 68, issue 11, pp. 6094-6100.
Kachlany, S.C., et al., "Purification of Secreted Laukotoxin (LtxA) from Actinobacillus antinomysetemcomitans," Protein Expr Purif, 2002, vol. 25, No. 3, pp. 465-471 (Abstract).
Kachlany, S. C., "Aggregatibacter Actinomycetemcomitans Leukotoxin: From Threat to Therapy," J. Dent Res, 2010, vol. 89, No. 6, pp. 561-570.
Kachlany, S. C. et al., "Anti-Leukemia Activity of a Bacterial Toxin With Natural Specificity for LFA-1 on White Blood Cells," Leuk Res, 2010, vol. 34, No. 6, pp. 777-785.
Mangan, D. F., et al., "Lethal Effects of Actinobacillus Actinomycetemcomitans Leukotoxin on Human T Lymphocytes," Infect Immun., Sep. 1991, vol. 59, No. 9, pp. 3267-3272.
Schechter, T., et al., "Pharmacokinetic disposition and clinical outcomes in infants and children receiving intravenous busulfan for allogeneic hematopoietic stem cell transplantation," Biol., Blood Marrow Transplant, Mar. 2007, vol. 13, No. 3, pp. 307-314 (Abstract).
Wang, Y., et al., "Effects of Imatinib (Glivec) on the Pharmacolinetics of Metoprolol, a CYP2D6 Substrate, in Chinese Patients with Chronic Myelogenous Laukaemia," B J Clin Pharmacol, 2008, vol. 65, No. 6, pp. 885-892.

* cited by examiner

*Primary Examiner* — Mary Lyons
(74) *Attorney, Agent, or Firm* — Fox Rothschild LLP

(57) ABSTRACT

The invention relates to pharmaceutical compositions comprising leukotoxin, a chemotherapeutic agent and a pharmaceutically acceptable carrier, including methods to treat cancer, and methods to induce apoptosis.

21 Claims, 4 Drawing Sheets

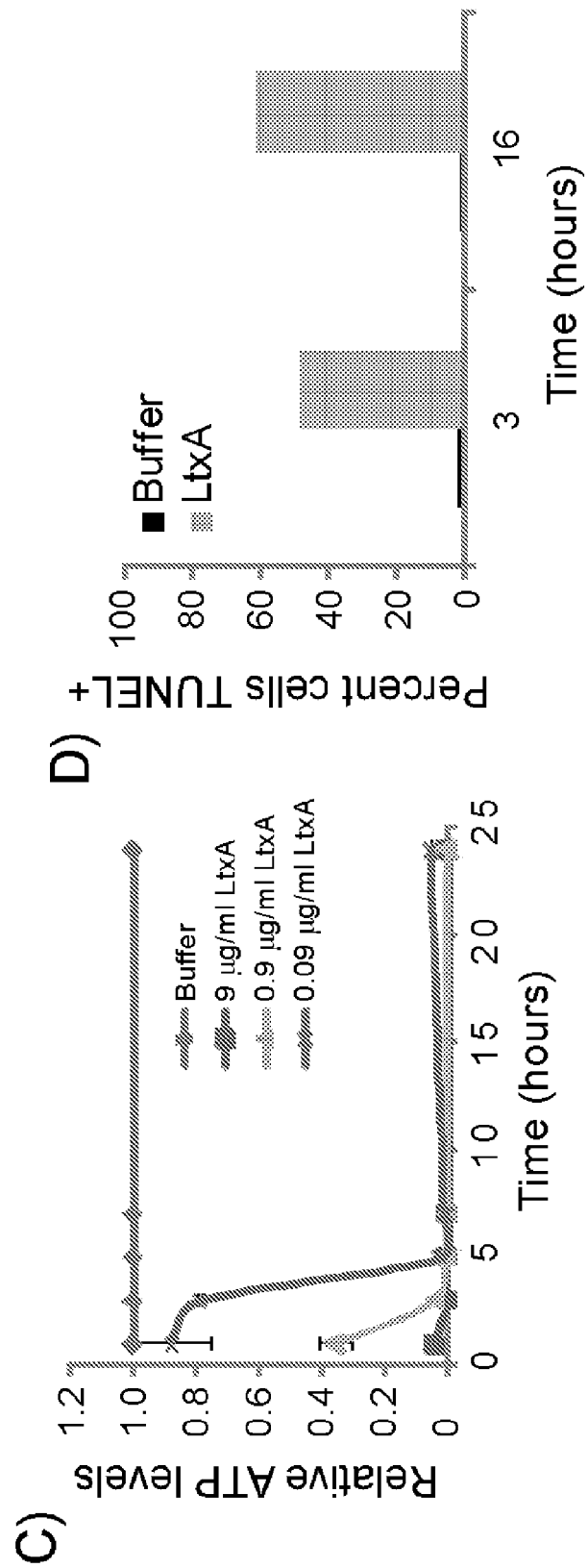

SEQUENCE LISTING

<160> NUMBER OF SEQ ID NOS: 2

<210> SEQ ID NO 1
<211> LENGTH: 1055
<212> TYPE: PRT
<213> ORGANISM: Aggregatibacter actinomycetemcomitans

<400> SEQUENCE: 1

```
Met Ala Thr Thr Ser Leu Leu Asn Thr Lys Gln Gln Ala Ala Gln Phe
1               5                   10                  15

Ala Asn Ser Val Ala Asp Arg Ala Lys Glu Asn Ile Asp Ala Ala Lys
            20                  25                  30

Glu Gln Leu Gln Lys Ala Leu Asp Lys Leu Gly Lys Thr Gly Lys Lys
        35                  40                  45

Leu Thr Leu Tyr Ile Lys Asn Tyr Lys Lys Gly Asn Gly Leu Thr Ala
    50                  55                  60

Leu Ile Lys Ala Ala Gln Lys Leu Gly Ile Glu Val Tyr His Glu Gly
65                  70                  75                  80

Lys Asp Gly Pro Ala Leu Thr Asn Gly Ile Leu Asn Thr Gly Lys Lys
                85                  90                  95

Leu Leu Gly Leu Thr Glu Arg Gly Leu Thr Leu Phe Ala Pro Glu Leu
            100                 105                 110

Asp Lys Trp Ile Gln Gly Asn Lys His Leu Ser Asn Ser Val Gly Ser
        115                 120                 125

Thr Gly Asn Leu Thr Lys Ala Ile Asp Lys Val Gln Ser Val Leu Gly
    130                 135                 140

Thr Leu Gln Ala Phe Leu Asn Thr Ala Phe Ser Gly Met Asp Leu Asp
145                 150                 155                 160

Ala Leu Ile Lys Ala Arg Gln Asn Gly Lys Asn Val Thr Asp Val Gln
                165                 170                 175

Leu Ala Lys Ala Ser Leu Asn Leu Ile Asn Glu Leu Ile Gly Thr Ile
            180                 185                 190

Ser Ser Ile Thr Asn Asn Val Asp Thr Phe Ser Lys Gln Leu Asn Lys
        195                 200                 205

Leu Gly Glu Ala Leu Gly Gln Val Lys His Phe Gly Ser Phe Gly Asp
    210                 215                 220

Lys Leu Lys Asn Leu Pro Lys Leu Gly Asn Leu Gly Lys Gly Leu Gly
225                 230                 235                 240

Ala Leu Ser Gly Val Leu Ser Ala Ile Ser Ala Ala Leu Leu Leu Ala
                245                 250                 255

Asn Lys Asp Ala Asp Thr Ala Thr Lys Ala Ala Ala Ala Ala Glu Leu
            260                 265                 270

Thr Asn Lys Val Leu Gly Asn Ile Gly Lys Ala Ile Thr Gln Tyr Leu
        275                 280                 285

Ile Ala Gln Arg Ala Ala Ala Gly Leu Ser Thr Thr Gly Pro Val Ala
    290                 295                 300

Gly Leu Ile Ala Ser Val Val Ser Leu Ala Ile Ser Pro Leu Ser Phe
305                 310                 315                 320

Leu Gly Ile Ala Lys Gln Phe Asp Arg Ala Arg Met Leu Glu Glu Tyr
                325                 330                 335

Ser Lys Arg Phe Lys Lys Phe Gly Tyr Asn Gly Asp Ser Leu Leu Gly
            340                 345                 350

Gln Phe Tyr Lys Asn Thr Gly Ile Ala Asp Ala Ala Ile Thr Thr Ile
        355                 360                 365
```

```
Asn Thr Val Leu Ser Ala Ile Ala Ala Gly Val Gly Ala Ser Ala
370                 375                 380

Gly Ser Leu Val Gly Ala Pro Ile Gly Leu Leu Val Ser Ala Ile Thr
385                 390                 395                 400

Ser Leu Ile Ser Gly Ile Leu Asp Ala Ser Lys Gln Ala Val Phe Glu
                405                 410                 415

His Ile Ala Asn Gln Leu Ala Asp Lys Ile Lys Ala Trp Glu Asn Lys
            420                 425                 430

Tyr Gly Lys Asn Tyr Phe Glu Asn Gly Tyr Asp Ala Arg His Ser Ala
        435                 440                 445

Phe Leu Glu Asp Ser Leu Lys Leu Phe Asn Glu Leu Arg Glu Lys Tyr
450                 455                 460

Lys Thr Glu Asn Ile Leu Ser Ile Thr Gln Gln Gly Trp Asp Gln Arg
465                 470                 475                 480

Ile Gly Glu Leu Ala Gly Ile Thr Arg Asn Gly Asp Arg Ile Gln Ser
                485                 490                 495

Gly Lys Ala Tyr Val Asp Tyr Leu Lys Lys Gly Glu Glu Leu Ala Lys
            500                 505                 510

His Ser Asp Lys Phe Thr Lys Gln Ile Leu Asp Pro Ile Lys Gly Asn
        515                 520                 525

Ile Asp Leu Ser Gly Ile Lys Gly Ser Thr Thr Leu Thr Phe Leu Asn
530                 535                 540

Pro Leu Leu Thr Ala Gly Lys Glu Glu Arg Lys Thr Arg Gln Ser Gly
545                 550                 555                 560

Lys Tyr Glu Phe Ile Thr Glu Leu Lys Val Lys Gly Arg Thr Asp Trp
                565                 570                 575

Lys Val Lys Gly Val Pro Asn Ser Asn Gly Val Tyr Asp Phe Ser Asn
            580                 585                 590

Leu Ile Gln His Ala Val Thr Arg Asp Asn Lys Val Leu Glu Ala Arg
        595                 600                 605

Leu Ile Ala Asn Leu Gly Ala Lys Asp Asp Tyr Val Phe Val Gly Ser
610                 615                 620

Gly Ser Thr Ile Val Asn Ala Gly Asp Gly Tyr Asp Val Val Asp Tyr
625                 630                 635                 640

Ser Lys Gly Arg Thr Gly Ala Leu Thr Ile Asp Gly Arg Asn Ala Thr
                645                 650                 655

Lys Ala Gly Gln Tyr Lys Val Glu Arg Asp Leu Ser Gly Thr Gln Val
            660                 665                 670

Leu Gln Glu Thr Val Ser Lys Gln Glu Thr Lys Arg Gly Lys Val Thr
        675                 680                 685

Asp Leu Leu Glu Tyr Arg Asn Tyr Lys Leu Asp Tyr Tyr Tyr Thr Asn
690                 695                 700

Lys Gly Phe Lys Ala His Asp Glu Leu Asn Ser Val Glu Glu Ile Ile
705                 710                 715                 720

Gly Ser Thr Leu Arg Asp Lys Phe Tyr Gly Ser Lys Phe Asn Asp Val
                725                 730                 735

Phe His Gly His Asp Gly Asp Leu Ile Tyr Gly Tyr Asp Gly Asp Asp
            740                 745                 750

Asp Arg Leu Tyr Gly Asp Asn Gly Asn Asp Glu Ile His Gly Gly Gln
        755                 760                 765

Gly Asn Asp Lys Leu Tyr Gly Ala Gly Asn Asp Arg Leu Phe Gly
770                 775                 780

Glu Tyr Gly Asn Asn Tyr Leu Asp Gly Gly Glu Gly Asp Asp His Leu
```

```
                            785                 790                 795                 800
                        Glu Gly Gly Asn Gly Ser Asp Ile Leu Arg Gly Gly Ser Gly Asn Asp
                                        805                 810                 815

Lys Leu Phe Gly Asn Gln Gly Asp Asp Leu Leu Asp Gly Gly Glu Gly
                                        820                 825                 830

Asp Asp Gln Leu Ala Gly Gly Glu Gly Asn Asp Ile Tyr Val Tyr Arg
                                        835                 840                 845

Lys Glu Tyr Gly His His Thr Ile Thr Glu His Ser Gly Asp Lys Asp
                            850                 855                 860

Lys Leu Ser Leu Ala Asn Ile Asn Leu Lys Asp Val Ser Phe Glu Arg
                        865                 870                 875                 880

Asn Gly Asn Asp Leu Leu Lys Thr Asn Asn Arg Thr Ala Val Thr
                                        885                 890                 895

Phe Lys Gly Trp Phe Ser Lys Pro Asn Ser Ser Ala Gly Leu Asp Glu
                                        900                 905                 910

Tyr Gln Arg Lys Leu Leu Glu Tyr Ala Pro Glu Lys Asp Arg Ala Arg
                                        915                 920                 925

Leu Lys Arg Gln Phe Glu Leu Gln Arg Gly Lys Val Asp Lys Ser Leu
                            930                 935                 940

Asn Asn Lys Val Glu Glu Ile Ile Gly Lys Asp Gly Glu Arg Ile Thr
                        945                 950                 955                 960

Ser Gln Asp Ile Asp Asn Leu Phe Asp Lys Ser Gly Asn Lys Lys Thr
                                        965                 970                 975

Ile Ser Pro Gln Glu Leu Ala Gly Leu Ile Lys Asn Lys Gly Lys Ser
                                        980                 985                 990

Ser Ser Leu Met Ser Ser Ser Arg  Ser Ser Ser Met Leu  Thr Gln Lys
                                        995                 1000                1005

Ser Gly  Leu Ser Asn Asp Ile  Ser Arg Ile Ile Ser  Ala Thr Ser
                                        1010                1015                1020

Gly Phe  Gly Ser Ser Gly Lys  Ala Leu Ser Ala Ser  Pro Leu Gln
                                        1025                1030                1035

Thr Asn  Asn Asn Phe Asn Ser  Tyr Ala Asn Ser Leu  Ala Thr Thr
                                        1040                1045                1050

Ala Ala
                            1055

<210> SEQ ID NO 2
<211> LENGTH: 3168
<212> TYPE: DNA
<213> ORGANISM: Aggregatibacter actinomycetemcomitans

<400> SEQUENCE: 2
atggcaacta cttcactgct aaatacaaaa cagcaagctg cacagtttgc aaattcagtt      60
gcagatagag ctaaggaaaa tattgatgct gcaaagaaac aattgcaaaa ggcgttagat     120
aaattaggga agacaggtaa gaaattaact ttatatatcc ctaagaatta caaaaaagga     180
aatggtctta ctgcgcttat aaaagcagca cagaagttag ggattgaagt atatcatgaa     240
gggaaagacg gcccggcatt aactaatggt atttttaaata ctgggaaaaa attacttggt     300
cttaccgaac gaggtttaac tttatttgct ccggaattag ataaatggat tcaaggtaat     360
aaacatttaa gtaattctgt gggtagtact ggaaatttga caaaagcgat agataaggtt     420
cagagtgttc ttggtacgtt acaagcgttt ttgaacaccg cattttcggg catggattta     480
gatgccttaa ttaaagcccg tcaaaatggt aaaaatgtaa cagatgtaca gctagcaaaa     540
```

```
gccagtctta aacctgattaa tgaattgatt ggtactattt ctagcattac aaataatgta    600 gatactttt ctaaacaact taataagtta ggtgaagcac taggacaagt aaaacatttt     660
ggtagttttg gagataaatt aaagaattta cctaagttag gtaatcttgg aaaaggttta   720
ggtgcattat ccggtgtatt gtcggctata tcagcggctc tattacttgc aaataaagat   780
gctgatactg caacgaaagc agcggctgca gctgaattga caaataaagt gctaggtaac   840
atcggtaaag cgatcacaca atacttgatt gctcaacgtg ctgcagcggg gctttctact   900
acgggacctg tcgcagggtt aattgcctct gtggtcagct tggcaatcag cccttttgtct  960 ttcctaggta ttgcgaaaca atttgatcgt gcgagaatgc ttgaggaata ctcgaaacgc  1020
tttaagaaat ttggttataa cggcgatagt ttacttggtc aattctacaa aaatacaggg  1080
atcgcagatg ctgcgattac aacgattaac actgtattaa gtgctattgc agcaggggtt  1140
ggtgcagcct ccgccggttc tttagttggt gcgccaatcg gtttgttagt gagtgcgatt  1200
accagcttaa tttcaggaat tcttgatgct tctaaacaag ccgttttga acatatcgcg   1260 aatcagctcg ccgataaaat taaagcatgg gagaataagt acggtaagaa ttactttgaa  1320
aatggctatg atgcccgtca ttccgccttc ttggaagatt cactaaaatt atttaatgag  1380
ttacgtgaaa aatataaaac cgaaaatata ttatctatca ctcaacaagg ttgggatcag  1440
cgcattggtg aattagcagg tatcactcgt aatggagatc gtattcaaag tggtaaagct  1500
tatgtggatt atttgaaaaa gggtgaggag cttgcaaagc atagcgataa attcactaaa  1560
cagattttag atccaatcaa aggtaatatt gatctttcgg gtataaaagg ttctaccact  1620
ctaacttttt taaatccgtt gttaaccgca ggtaaggaag aacggaaaac acgtcagtca  1680
ggtaaatatg aatttattac tgaattaaaa gtaaaaggac gtaccgattg gaaggtaaaa  1740
ggtgttccta attctaatgg tgtatatgat ttttctaact taattcaaca tgccgttaca  1800
cgtgataata aagttctaga agcaagatta attgctaatt tgggtgctaa agatgattat  1860 gttttgtcg gatccggttc aacaatagtt aatgctggag acggttatga tgtggtggac  1920
tatagtaaag gtcgcaccgg tgcattaaca atcgacggtc gtaatgctac taaagccgga  1980
caatataagg ttgaaagaga tcttagcggt actcaagtct tgcaggaaac cgtatcaaag  2040
caagaaacta aacgagggaa ggttaccgat ctacttgaat atcgtaacta taaattagat  2100
tactattata cgaataaggg ctttaaagct catgatgaat taaactcagt agaggaaatt  2160
atcggcagca cactacgtga taaatttat ggttctaaat ttaatgatgt tttccatggt  2220
cacgatggcg atgatttgat ttatggttat gatggcgatg atcgtttgta tggcgataat  2280
gggaatgacg aaattcatgg cggccaaggt aatgataagc tctatggtgg tgccggtaac  2340
gataggctct ttggtgaata tggcaacaac tatcttgacg gtggagaagg cgacgaccac  2400
ttagagggag gcaatggttc cgatattcta agaggtggaa gtggcaatga taagttgttt   2460
ggaaaccaag gagatgattt acttgacggt ggagaaggcg atgaccaact tgccggtgga  2520
gaaggaaatg atatttatgt ttaccgtaaa gaatatgggc accacactat tacgaacat   2580 agcggtgata aagataaatt atcattagca aatatcaatc tcaaagatgt gtcatttgag  2640
cgtaacggca atgatctact attgaaaaca aataatagaa cagcagtaac atttaaagga  2700
tggtttagta aacctaattc atcggcagga ttagatgagt atcaaagaaa acttcttgaa  2760
tacgcacctg aaaaggatcg tgcacgactt aagagacaat ttgagttaca gcgaggtaaa  2820
gtcgacaaat cactcaataa taagttgaa gaaattatcg gtaaagatgg ggagcggatt  2880
acttcgcaag acattgataa tctttttgat aagagtggga acaaaaagac aatttcacct  2940
```

```
caagagcttg ccggacttat taagaataaa ggtaagtcaa gtagccttat gtcttcttct    3000
cgttcgtcaa gtatgcttac acaaaagtcc ggtttgtcaa atgatattag tcgtattatt    3060
tcagcaacca gtggttttgg ttcatccggt aaagcgttat ccgcttcgcc attgcagacc    3120
aataataact ttaactctta cgcaaattcg ttagcaacta ctgcggcc                 3168
```

COMBINATION THERAPY WITH LEUKOTOXIN

CROSS REFERENCE TO RELATED APPLICATION

This application is the U.S. National Phase of International Patent Application Serial No. PCT/US12/29476, filed Mar. 16, 2012, which claims priority of U.S. Provisional Application No. 61/453,162 filed on Mar. 16, 2011. The content of the foregoing applications are incorporated herein by reference in their entireties.

FIELD OF THE INVENTION

The invention relates to pharmaceutical compositions comprising leukotoxin, a chemotherapeutic agent and a pharmaceutically acceptable carrier, including methods to treat cancer, and methods to induce apoptosis.

BACKGROUND OF THE INVENTION

Leukotoxin (LtxA) is a bacterial protein, an experimental therapeutic that binds leukocyte function antigen (LFA-1) on white blood cells (WBCs) and induces cell death via apoptosis or necrosis. LtxA is secreted by the oral bacterium, *Aggregatibacter actinomycetemcomitans*. It has been found that LtxA preferentially targets WBCs with high levels of activated LFA-1, a characteristic of many leukemias and lymphomas.

The U.S. FDA recently issued an initiative and draft guidelines to promote the development of experimental therapeutics in combination to improve the efficacy and safety profile of cancer drug regimens because many of the standard chemotherapeutic agents are highly cytotoxic that elicit severe side effects. Thus, there remains a need to develop new cancer drugs and therapy that are less toxic and effective to treat cancer.

SUMMARY OF THE INVENTION

The invention relates to pharmaceutical compositions comprising leukotoxin, a chemotherapeutic agent and a pharmaceutically acceptable carrier, including methods to treat cancer, and methods to induce apoptosis.

In one aspect, the invention provides pharmaceutical compositions containing leukotoxin, at least one other chemotherapeutic agent, and a pharmaceutically acceptable carrier. The chemotherapeutic agent may be a topoisomerase II inhibitor, a DNA alkylating agent, or a BCR-ABL inhibitor. In certain embodiments, the topoisomerase II inhibitor is etoposide, mitoxantrone, or daunorubicin or pharmaceutically acceptable salts thereof. In another embodiment, the DNA alkylating agent is busulfan. In another embodiment, the BCR-ABL inhibitor is imatinib or imatinib mesylate.

In a second aspect, the invention provides methods for inducing apoptosis of a cancer cell, comprising contacting the cell with leukotoxin and at least one other chemotherapeutic agent in amounts effective to induce apoptosis. The chemotherapeutic agent may be a topoisomerase II inhibitor, a DNA alkylating agent, or a BCR-ABL inhibitor. In certain embodiments, the topoisomerase II inhibitor is etoposide, mitoxantrone, or daunorubicin or pharmaceutically acceptable salts thereof. In another embodiment, the DNA alkylating agent is busulfan. In another embodiment, the BCR-ABL inhibitor is imatinib or imatinib mesylate. In certain embodiments, the leukotoxin and the other chemotherapeutic agent are contacted with the cell simultaneously or sequentially. In other embodiments, the cancer cell expresses leukocyte function antigen (LFA-1). In certain embodiments, the cancer cell is a hematological cancer cell, and may be a leukemia cell, a lymphoma cell, or a myeloma cell.

In a third aspect, the invention provides methods for treating a hematological cancer in a subject in need of such treatment comprising administering effective amounts of leukotoxin and at least one chemotherapeutic agent to said subject. The chemotherapeutic agent may be a topoisomerase II inhibitor, a DNA alkylating agent, or a BCR-ABL inhibitor. In certain embodiments, the topoisomerase II inhibitor is etoposide, mitoxantrone, or daunorubicin or pharmaceutically acceptable salts thereof. In another embodiment, the DNA alkylating agent is busulfan. In another embodiment, the BCR-ABL inhibitor is imatinib or imatinib mesylate. In certain embodiments, the leukotoxin and the other chemotherapeutic agent are administered to the subject simultaneously or sequentially. The hematological cancer may be leukemia, lymphoma, or myeloma.

In a fourth aspect, the invention provides kits embodying a pharmaceutically acceptable dose unit of a pharmaceutically effective amount of leukotoxin, and a pharmaceutically acceptable dose unit of a pharmaceutically effective amount of a chemotherapeutic agent. The two pharmaceutically acceptable dose units can optionally take the form of a single pharmaceutically acceptable dose unit. The chemotherapeutic agent may be a topoisomerase II inhibitor, a DNA alkylating agent, or a BCR-ABL inhibitor. In certain embodiments, the topoisomerase II inhibitor is etoposide, mitoxantrone, or daunorubicin or pharmaceutically acceptable salts thereof. In another embodiment, the DNA alkylating agent is busulfan. In certain embodiments, the BCR-ABL inhibitor is imatinib or imatinib mesylate.

BRIEF DESCRIPTION OF THE DRAWINGS

FIGS. 1A-D shows the mechanism of THP-1 cell killing by LtxA: FIG. 1A—depicts apoptosis measured by binding of annexin V-FITC to cells, determined by flow cytometry; FIG. 1B illustrates staining of cells using the JC-1 dye; FIG. 1C—depicts depletion of cellular ATP by LtxA over time, measured using the CellTiter Glo ATP viability assay; FIG. 1D—shows fragmentation of chromosomal DNA measured by the TUNEL assay and flow cytometry after treatment with 1.0 µg/ml LtxA;

DETAILED DESCRIPTION OF THE INVENTION

1. Overview

Figure 1A:
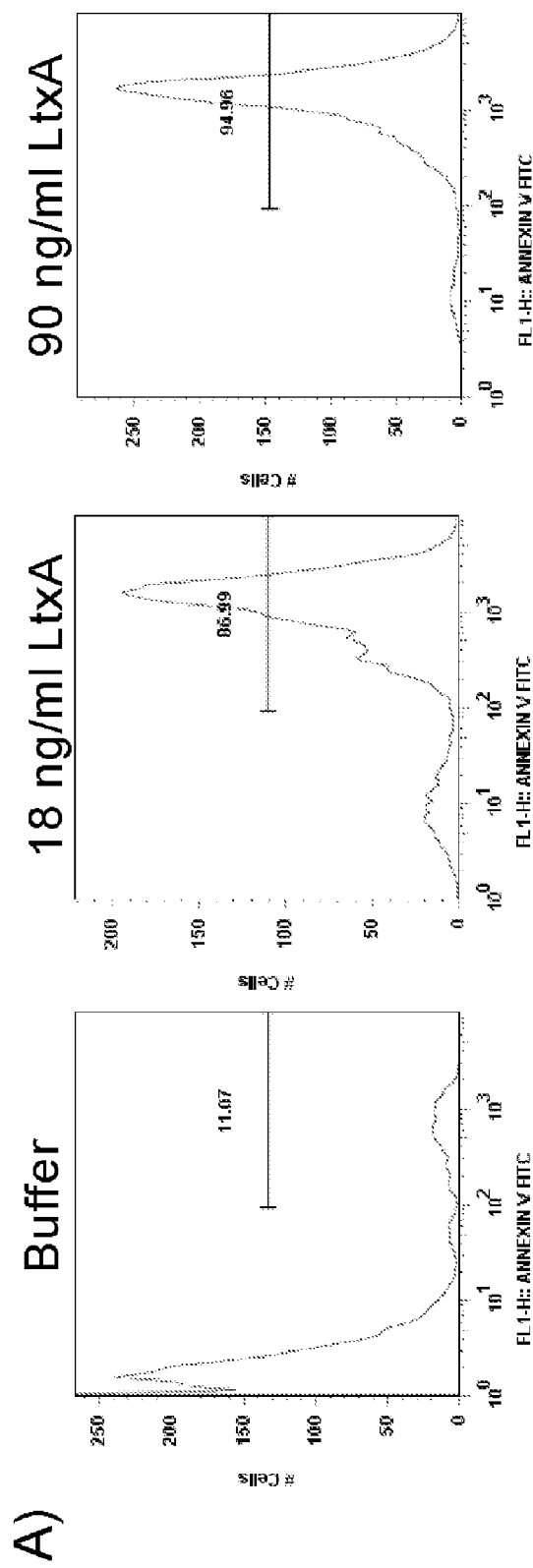

The invention relates to pharmaceutical compositions comprising leukotoxin, a chemotherapeutic agent and a pharmaceutically acceptable carrier, including methods to treat cancer, and methods to induce apoptosis.

LtxA is a ~115 kDa protein produced by the Gram negative bacterium *Aggregatibacter actinomycetemcomitans* (Kachlany, S. C. 2010. *J Dent Res* 89:561-570.). LtxA specifically kills leukocytes of humans and old world primates by forming pores in the membrane and causing apoptosis or necrosis (Mangan et al., 1991. *Infect Immun* 59:3267-72.). LtxA binds specifically to LFA-1 and cells that lack LFA-1 are resistant to its toxicity (Kachlany, S. C. et al., 2010.

*Leukemia Research* 34:777-85.). For example, LtxA is not active against human red blood cells, human epithelial cells, rat cells, or mouse cells. LtxA also remains active in the presence of human peripheral blood. While many LtxA preparations can be used, highly purified LtxA is preferred.

Examples include LtxA polypeptide purified from *Aggregatibacter actinomycetemcomitans* (SEQ ID NO: 1) and other variants having substantially the same biological activity as that having the sequence of SEQ ID NO: 1. It was discovered that *Aggregatibacter actinomycetemcomitans* secreted active LtxA into culture supernatants (Kachlany, S. C., et al. 2000. Infect Immun 68:6094-100) and an efficient method for its purification was described in Kachlany, S. C., et al. 2002. *Protein Expr Purif* 25:465-71. This method can therefore be used to prepare isolated or purified LtxA polypeptide. In one example, a purification procedure of the toxin involves:
  a. inoculating a single colony of *Aggregatibacter actinomycetemcomitans* into a fresh broth and growing cultures;
  b. adding the growing cultures to fresh broth, adding glass beads and incubating;
  c. centrifuging the incubated culture, forming a pellet and a supernatant;
  d. filtering the supernatant through a membrane to provided a filtered supernatant;
  e. mixing $(NH_4)_2SO_4$ and the filtered supernatant together to form a mixture;
  f. centrifuging the mixture to form a mixture pellet;
  g. resuspending the mixture pellet in buffer to form a protein resuspension;
  h. passing the protein resuspension through a column; and
  i. collecting the protein eluting off the column.

See also PCT/US2006/45258 (WO 2007/062150) and US Application 20090075883 (U.S. Ser. No. 12/154,843). The contents of these two documents are incorporated herein by reference in their entireties.

An "isolated polypeptide" refers to a polypeptide that has been separated from other proteins, lipids, and nucleic acids with which it is naturally associated. The polypeptide can constitutes at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A functional equivalent of LtxA refers to a polypeptide derivative of the LtxA polypeptide, e.g., a protein having one or more point mutations, insertions, deletions, truncations, a fusion protein, or a combination thereof. It retains substantially the activity of the LtxA polypeptide, i.e., the ability to target and kill WBCs that express the activated conformation of LFA-1 on their surface while having little or no toxic effect on other cells or organs in the body. The isolated polypeptide can contain SEQ ID NO: 1 or a functional fragment of SEQ ID NO: 1. In general, the functional equivalent is at least 75% (e.g., any number between 75% and 100%, inclusive, e.g., 70%, 80%, 85%, 90%, 95%, and 99%) identical to SEQ ID NO: 1.

All of naturally occurring LtxA, genetically engineered LtxA, and chemically synthesized LtxA can be used to practice the invention disclosed herein. LtxA obtained by recombinant DNA technology may have the same amino acid sequence as naturally a occurring LtxA (SEQ ID NO: 1) or a functionally equivalent thereof. The term "LtxA" also covers chemically modified LtxA. Examples of chemically modified LtxA include LtxA subjected to conformational change, addition or deletion of a sugar chain, and LtxA to which a compound such as polyethylene glycol has been bound. Once purified and tested by standard methods known in the art, LtxA can be included in a pharmaceutical composition.

The amino acid composition of the LtxA polypeptide described herein may vary without disrupting the ability of the polypeptide to target and kill WBCs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to improve skin condition to identify mutants that retain the activity as described below in the examples.

A LtxA polypeptide as described in this invention can be obtained as a naturally occurring polypeptide or a recombinant polypeptide. To prepare a recombinant polypeptide, a nucleic acid encoding it (e.g., SEQ ID NO: 2) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

2. Definitions

As used herein, the singular forms "a," "an" and "the" include plural references unless the content clearly dictates otherwise.

The term "about", as used here, refers to +/−10% of a value.

The term "amino acid" refers to natural and/or unnatural or synthetic amino acids, including glycine and both the D and L optical isomers, amino acid analogs (for example norleucine is an analog of leucine) and peptidomimetics.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "effective amount," "therapeutically effective amount" or "therapeutic effect" refers to an amount of an antibody, polypeptide, polynucleotide, small organic molecule, or other drug effective to "treat" a disease or disorder in a subject or mammal. In the case of cancer, the therapeutically effective amount of the drug has a therapeutic effect and as such can reduce the number of cancer cells; decrease tumorgenicity, tumorigenic frequency or tumorigenic capacity;

reduce the number or frequency of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer; reduce morbidity and mortality; improve quality of life; or a combination of such effects.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. In certain embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity; reduction in the number or frequency of cancer cells; or some combination of effects.

3. Pharmaceutical Compositions and Methods of Use

The invention provides pharmaceutical compositions comprising leukotoxin, at least one other chemotherapeutic agent, and a pharmaceutically acceptable carrier. In general, the chemotherapeutic agents are antineoplastic agents used to treat cancer, including without limitation topoisomerase II inhibitors, DNA alkylating agents, and BCR-ABL inhibitors.

Alkylating agents (used interchangeably with DNA alkylating agents) are so named because of their ability to alkylate many nucleophilic functional groups under conditions present in cells. Cisplatin and carboplatin, as well as oxaliplatin, are alkylating agents. They impair cell function by forming covalent bonds with the amino, carboxyl, sulfhydryl, and phosphate groups in biologically important molecules. Other agents include busulfan, mechlorethamine, cyclophosphamide, chlorambucil, ifosfamide and pharmaceutically acceptable salts thereof. They work by chemically modifying a cell's DNA.

In certain embodiments, the DNA alkylating agent is busulfan.

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, etoposide, mitoxantrone, daunorubicin, teniposide and pharmaceutically acceptable salts thereof, including mitoxantrone HCl and daunorubicin HCl In certain embodiments, the topoisomerase II inhibitor is etoposide, mitoxantrone, mitoxantrone HCl, daunorubicin or daunorubicin HCl.

Bcr-Abl tyrosine-kinase inhibitors (TKI) (used interchangeably with BCR-ABL inhibitors) are the first-line therapy for most patients with chronic myelogenous leukemia (CML). In more than 90% of cases, CML is caused by chromosomal abnormality resulting in the formation of a so-called Philadelphia chromosome. This abnormality is due to fusion between Abelson (Abl) tyrosine kinase gene at chromosome 9 and break point cluster (Bcr) gene at chromosome 22, resulting in the chimeric oncogene Bcr-Abl and a constitutively active Bcr-Abl tyrosine kinase that has been implicated in the pathogenesis of CML. Compounds have been developed that selectively inhibit this tyrosine kinase. Examples of Bcr-Abl tyrosine-kinase inhibitors (TKI) include without limitation, imatinib, nilotinib, bosutinib, ponatinib, bafetinib, and pharmaceutically acceptable salts thereof, including imatinib mesylate.

In certain embodiments, the BCR-ABL inhibitor is imatinib or imatinib mesylate.

To administer the pharmaceutical composition to a subject, it is preferable to formulate the molecules in a composition comprising one or more pharmaceutically acceptable carriers. The phrase "pharmaceutically acceptable" refers to molecular entities and compositions that do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like.

The carrier may be formed of any suitable pharmaceutically acceptable or therapeutically acceptable material, which are well known. The carrier may comprise of a metal, glass, lipid, protein, polymer or any combinations thereof.

In a preferred embodiment, the carrier is a particle formed from biocompatible or biodegradable polymers such as polylactic and/or polyglycolic acids, polyanhydrides, polycaprolactones, polyethylene oxides, polybutylene terephthalates, starches, cellulose, chitosan, and/or combinations of these. The particles may comprise a hydrogel, such as agarose, collagen, or fibrin.

Non-biodegradable or biodegradable polymers may be used to form the particles. In the preferred embodiment, the particles are formed of a biodegradable polymer. In general, synthetic polymers are preferred, although natural polymers may be used and have equivalent or even better properties, especially some of the natural biopolymers which degrade by hydrolysis, such as some of the polyhydroxyalkanoates. Representative synthetic polymers include poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and poly-propylene, polyalkylene glycols such as poly (ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), poly-vinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-capro-lactone), copolymers and blends thereof. As used herein, "derivatives" include polymers having substitutions, additions of chemical groups and other modifications routinely made by those skilled in the art.

Examples of preferred biodegradable polymers include polymers of hydroxy acids such as lactic acid and glycolic acid, and copolymers with PEG, polyanhydrides, poly(ortho) esters, polyurethanes, poly(butyric acid), poly(valeric acid), poly(lactide-co-capro-lactone), blends and copolymers thereof.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

4. Methods for Inducing Apoptosis

The invention provides methods for inducing apoptosis of a cancer cell comprising contacting the cell with leukotoxin and at least one other chemotherapeutic agent in amounts effective to induce apoptosis. The other chemotherapeutic agents include without limitation topoisomerase II inhibitors, DNA alkylating agents, and BCR-ABL inhibitors. In certain embodiments, the DNA alkylating agent is busulfan. In certain embodiments, the topoisomerase II inhibitor is etoposide, mitoxantrone, or daunorubicin. In certain embodiments, the BCR-ABL inhibitor is imatinib.

The cells treated with leukotoxin and at least one other chemotherapeutic agent are cells that express leukocyte function antigen (LFA-1). The cells are generally considered to be hematological cancer cells, cancer related to white blood cells. Examples of hematological cancer cells include without limitation, leukemia, lymphoma, and myeloma. Leukemias include acute myeloid leukemia, chronic myeloid leukemia, acute lymphocytic leukemia and chronic lymphocytic leukemia. Lymphomas include Hodgkin lymphoma, non-Hodgkin lymphoma, mantle cell lymphoma, diffuse large-b-cell lymphoma, and follicular lymphoma. Myelomas include multiple myeloma, extramedullary plasmacytoma, plasmacytomas, and solitary myeloma. Other types of hematological cancer cells are known by one with ordinary skill in the art.

5. Methods for Treating a Hematological Cancer

The invention also provides methods for treating a hematological cancer in a subject in need of such treatment comprising administering effective amounts of leukotoxin and at least one other chemotherapeutic agent to said subject. Leukotoxin and the chemotherapeutic agent may be administered to the subject simultaneously, sequentially and/or according to a regimen prescribed by a clinician. For example, on Day 1, Leukotoxin and the chemotherapeutic agent may be administered to the subject simultaneously; Day 2 leukotoxin is administered to the subject; Day 3 the chemotherapeutic agent is administered to the agent; Day 4, Leukotoxin and the chemotherapeutic agent may be administered to the subject simultaneously again, beginning a new regimen.

The other chemotherapeutic agents include without limitation topoisomerase II inhibitors, DNA alkylating agents, and BCR-ABL inhibitors. In certain embodiments, the DNA alkylating agent is busulfan. In certain embodiments the topoisomerase II inhibitor is etoposide, mitoxantrone, mitoxantrone HCl, daunorubicin, or daunorubicin HCl. In certain embodiments, the BCR-ABL inhibitor is imatinib or imatinib mesylate.

The hematological cancer may be leukemia, lymphoma, or myeloma Leukemias include acute myeloid leukemia, chronic myeloid leukemia, acute lymphocytic leukemia and chronic lymphocytic leukemia. Lymphomas include Hodgkin lymphoma, non-Hodgkin lymphoma, mantle cell lymphoma, diffuse large-b-cell lymphoma, and follicular lymphoma. Myelomas include multiple myeloma, extramedullary plasmacytoma, plasmacytomas, and solitary myeloma. Other types of hematological cancers are known by one with ordinary skill in the art. In certain embodiments, the hematological cancer is leukemia, lymphoma, myeloma, or any combination thereof. Generally, the cancer also expresses LFA-1.

Depending on the nature of the cancer, the pharmaceutical compositions of the instant invention may be administered by routes independently selected from the group consisting of oral administration, intravenous administration, intraarterial administration, intramuscular administration, intracolonic administration, intracranial administration, intrathecal administration, intraventricular administration, intraurethral administration, intravaginal administration, subcutaneous administration, intraocular administration, intranasal administration, and any combinations thereof.

In the present specification, parenteral includes subcutaneous injection, intravenous injection, intramuscular injection, intraperitoneal injection, drip or topical administration (transdermal administration, transocular administration, transpulmonary or bronchial administration, transnasal administration, transrectal administration and the like) and the like.

The dose of the pharmaceutical composition of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, it is parenterally administered at, for example, 0.01 to 100 mg/patient/day by subcutaneous, intravenous, intramuscular, transdermal, transocular, transpulmonary bronchial, or transnasal administration.

Oral dosage forms may include capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In particular examples, an oral dosage range is from about 1.0 to about 100 mg/kg body weight administered orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated.

6. Kits Containing Leukotoxin and a Chemotherapeutic Agent

In another aspect, the invention provides kits comprising a pharmaceutically acceptable dose unit of a pharmaceutically effective amount of leukotoxin, and a pharmaceutically acceptable dose unit of a pharmaceutically effective amount of a chemotherapeutic agent. The two pharmaceutically acceptable dose units can optionally take the form of a single pharmaceutically acceptable dose unit.

The other chemotherapeutic agents include without limitation topoisomerase II inhibitors, DNA alkylating agents, and BCR-ABL inhibitors. In certain embodiments, the DNA alkylating agent is busulfan. In certain embodiments, the topoisomerase II inhibitor is etoposide, mitoxantrone, mitoxantrone HCl, daunorubicin, or daunorubicin HCl. In certain embodiments, the BCR-ABL inhibitor is imatinib or imatinib mesylate.

The kits of the invention may further comprise a set of instructions that provide guidance on the use of the dose units for treatment of a hematologic cancer by simultaneous or sequential administration.

EXAMPLES

The invention now being generally described, it will be more readily understood by reference to the following examples, which are included merely for purposes of illustration of certain aspects and embodiments of the present invention, and are not intended to limit the invention.

Materials and Methods

Cell lines. THP-1 (acute monocytic leukemia), HL-60 (acute promyelocytic leukemia), GDM-1 (myelomonoblastic leukemia), and KU-812 (chronic myelogenous leukemia) cells were obtained from ATCC (Manassas, Va.) and maintained in RPMI 1640 medium with 10% fetal bovine serum (Invitrogen, Carlsbad, Calif.) at 37° C., 5% $CO_2$.

Primary cells. Frozen primary human cells were purchased from AllCells, LLC. (Emeryville, Calif.). Viability of these primary cells was >90%.

Purification of LtxA. Leukotoxin (LtxA) was purified from culture supernatants of *A. actinomycetemcomitans* strain NJ4500 as previously described in Diaz R, et al. Microb Pathog. 2006; 40:48-55 and Kachlany S C, et al. Protein Expr Purif. 2002; 25:465-471. All toxin preparations were filtered through a 0.22 µm filter prior to use. Concentration of protein was determined using the BCA protein assay using bovine serum albumin to generate a standard curve (Thermo Scientific, Rockford, Ill.).

Standard cytotoxic drugs. Busulfan, imatinib mesylate, etoposide, mitoxantrone HCl, and daunorubicin HCl were purchased from Easy Buyer Ltd. (Shanghai, China) and resuspended in DMSO. Stock solutions of 20 mg/ml were prepared for each drug. Serial dilutions were made in serum free medium.

Cell staining and flow cytometry. LtxA-induced apoptosis was measured by staining cells with annexin V-FITC according to the manufacturer's instructions (Biolegend, San Diego, Calif.) and analyzing cells using flow cytometry on a BD FACSCalibur instrument (BD Biosciences, Franklin Lakes, N.J.). To detect breakdown of the mitochondrial membrane potential, cells were stained with the cationic dye, 5,5',6,6'-tetrachloro-1,1',3,3'-tetraethylbenzimidazolylcarbocyanine iodide (JC-1) according to the supplier's instructions (Cell Technology, Mountain View, Calif.) and analyzed by flow cytometry. For all flow cytometry studies, at least 10,000 cells were analyzed per sample. Data was analyzed using FlowJo software (Ashland, Oreg.).

ATP depletion assay. ATP depletion caused by LtxA was measured in THP-1 cells ($10^6$ cells/ml) and primary cell samples ($10^6$ cells/ml) using the CellTIter-Glo luminescent cell viability assay (Promega, Madison, Wis.) according to the manufacturer's instructions. Plates were read in a Synergy HT plate reader in the luminescence mode (Bio-Tek, Winooski, Vt.). ATP depletion assays were performed in triplicate.

DNA fragmentation assay. The TUNEL assay was carried out using the TUNEL assay kit according to the supplier's instructions (Guava Technologies, Hayward, Calif.). The assay measures the amount of TRITC-conjugated anti-BrdU that labels nick-ended DNA. Apoptotic cells are represented by TUNEL positive (labeled) cells by flow cytometery. At least 10,000 cells were analyzed per sample.

Evaluation of drug combinations. For drug combination studies, cell lines (THP-1, HL-60, GDM-1, and KU-812) were seeded in triplicate at a density of $10^4$ cells/well of a 96-well plate and grown overnight. LtxA and drugs were then added and the plate was incubated for 48 hours. Vehicle-treated cells served as controls. Cytotoxicity was evaluated using the MTT assay as described in Mosmann T. Journal of immunological methods. 1983; 65:55-63. The percentage cytotoxicity after treatment was calculated using equation 1:

$$\% \text{ inhibition} = (1 - X/R) \times 100 \qquad \text{(Equation 1)}$$

X=Mean absorbance of treated cells
R=Mean absorbance of vehicle-treated cells
The combination index (CI) was calculated at the IC50 values according to as shown in equation 2:

$$CI(x) = \frac{DLtxA(x) + Dy(x) + DLtxA(x) \times Dy(x)}{ICLtxA(x)ICy(x)ICLtxA(x) \times ICy(x)} \qquad \text{(Equation 2)}$$

DLtxA (x)=Concentration of LtxA in combination to produce x percentage cytotoxicity.
Dy (x)=Concentration of chemotherapeutic drug in combination to produce x percentage cytotoxicity.
ICLtxA (x)=Concentration of LtxA to produce x percentage cytotoxicity determined using GraphPad Prism software (GraphPad Software, Inc., La Jolla, Calif.).
ICy (x)=Concentration of chemotherapeutic drug to produce x percentage cytotoxicity determined using GraphPad Prism software (GraphPad Software, Inc., La Jolla, Calif.).

Results

Figure 1B:
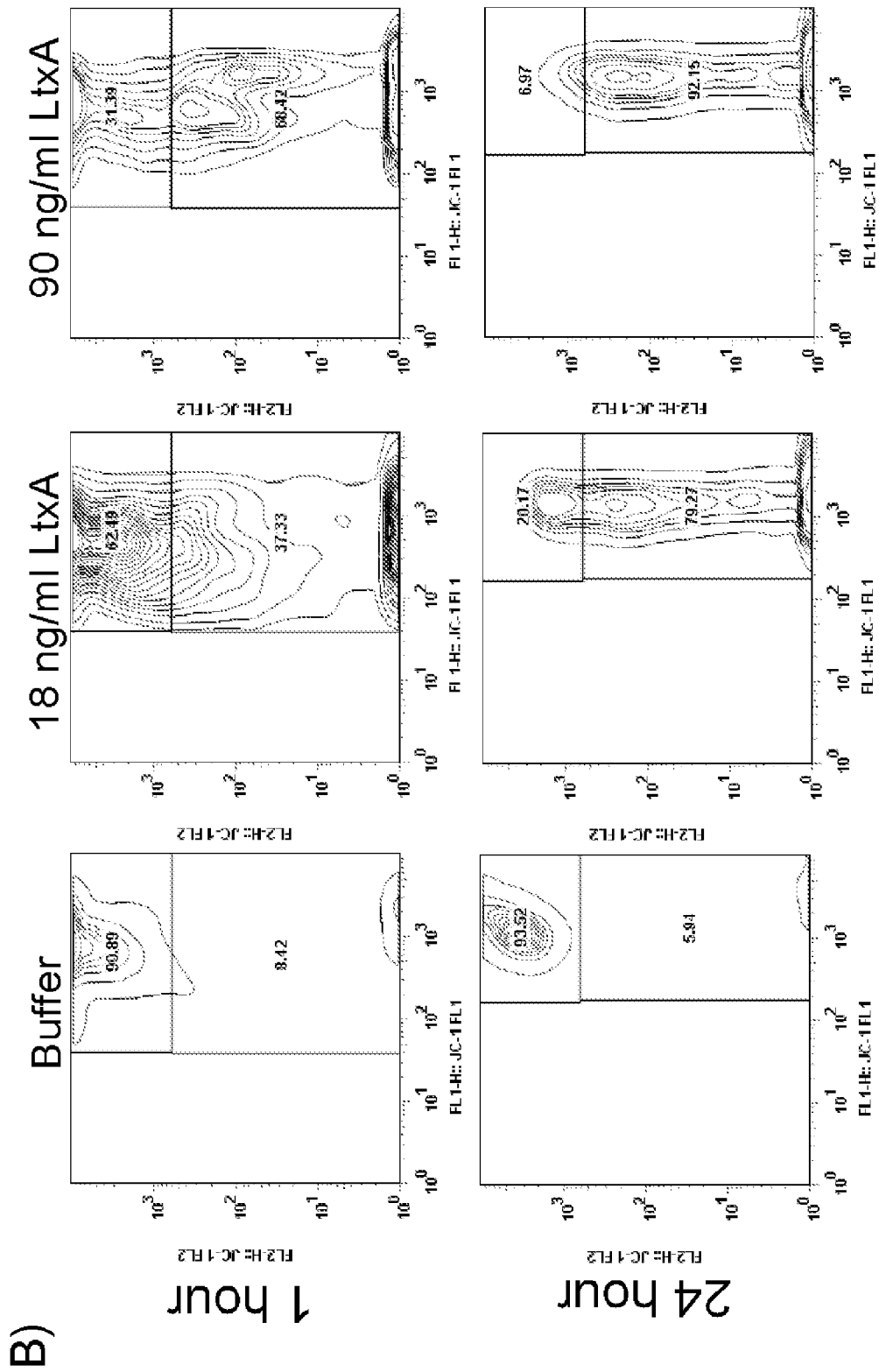
Figure 2:
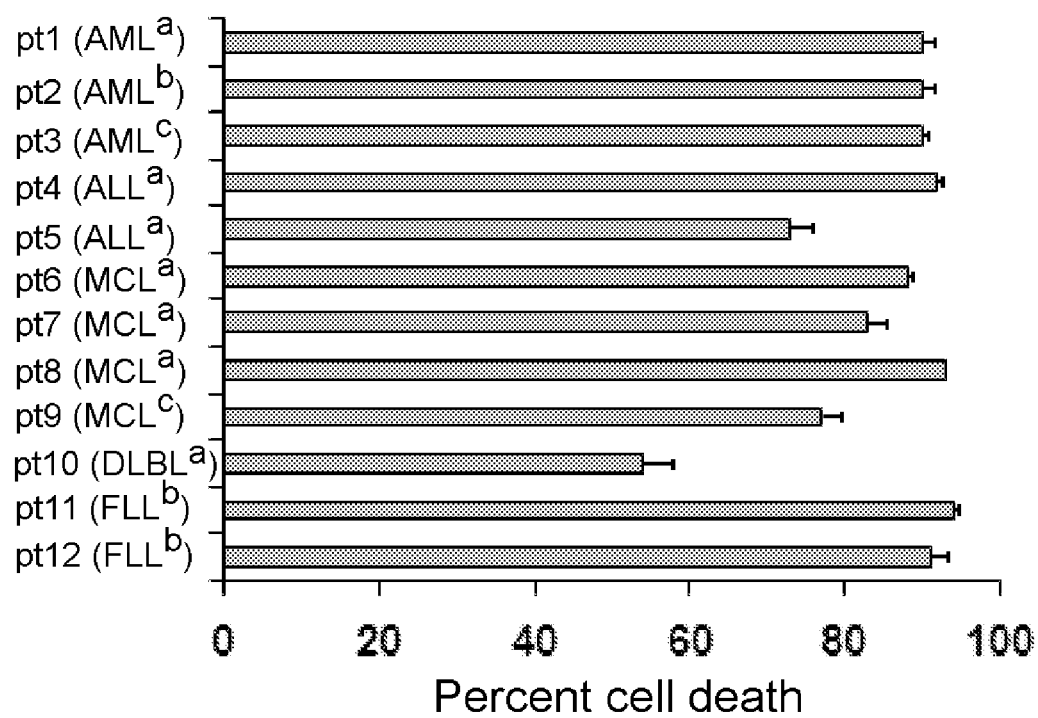
FIG. 2 illustrates the susceptibility of primary leukemia and lymphoma cells to LtxA when peripheral blood mononuclear cells (PBMCs) were treated with 2 µg/ml LtxA for 24 hours.

Characterization of LtxA-mediated cell killing. Cell killing was analyzed in several ways including translocation of phosphatidylserine from the inner to the outer leaflet of the plasma membrane (annexin V staining), collapse of the mitochondrial membrane potential, depletion of cellular ATP, and fragmentation of nuclear DNA. Apoptosis was measured by staining cells with annexin V and performing flow cytometry (FIG. 1A). After one hour with 18 ng/ml LtxA, approximately 87% of the cells were annexin V positive while approximately 95% of the cells were positive with 90 ng/ml LtxA. We used the JC-1 dye was used, which signals the collapse of the electrochemical gradient across the mitochondrial membrane and results in a decrease in red fluorescence. Treatment of THP-1 cells with LtxA caused rapid loss in the mitochondrial membrane potential and the effect was time- and dose-dependent (FIG. 1B). LtxA caused rapid depletion of cellular ATP, which was also time- and dose dependent (FIG. 1C). By 5 hours with 90 ng/ml LtxA, nearly all of the ATP had been depleted from cells and the effect occurred earlier with higher concentrations of LtxA (FIG. 1C). Another hallmark feature of apoptosis is fragmentation of nuclear DNA. Cells were analyzed using the TUNEL assay and flow cytometry (FIG. 1D). After 3 hours of LtxA treatment, approximately 50% of the cells were TUNEL positive and this value increased to 61% after 16 hours. The data indicates that LtxA induces very rapid cellular apoptosis, even at relatively low doses.

Combination cytotoxicity studies. Leukemia cell lines were incubated in different combinations of LtxA and other chemotherapeutic agents for 48 hours and then the percentage cytotoxicity was measured using the MTT assay. The combination index (CI) was calculated for drugs alone and in combination using the formula described in Materials and Methods. CI values were interpreted as described: <0.1, very strong synergy; 0.1-0.3, strong synergy; 0.3-0.7, synergy; 0.7-0.9, moderate synergy; 0.9-1.1, nearly additive; 1.1-1.45, moderate antagonism; 1.45-3.3, antagonism; >3.3, strong antagonism. A combination index of 0.1 indicates that only 5% of LtxA and the drug combined are needed to achieve the same result as either alone.

Etoposide. Three AML cell lines were tested with etoposide, THP-1, GDM-1, and HL-60. The Cmax of etoposide is 33.9 µM (Kaul S, et al. J Clin Oncol. 1995; 13:2835-2841). THP-1 cells revealed synergy between LtxA and etoposide at 0.01 µg/ml LtxA and values in the range of the Cmax for etoposide. At 0.1 µg/ml LtxA, strong synergy was observed. Both GDM-1 and HL-60 cells revealed very strong synergy at the lowest doses of LtxA tested (0.01 µg/ml and 0.1 µg/ml, respectively).

| (A) Etopside (µM) | | | | | |
|---|---|---|---|---|---|
| LtxA (µg/ml) | 0.17 | 1.7 | 16.99 | 84.95 | 169.91 |
| 0.01 | 1.893 | 1.893 | 0.643 | 0.606 | 0.604 |
| 0.1 | 1.452 | 1.452 | 0.203 | 0.165 | 0.163 |
| 1.0 | 1.544 | 1.544 | 0.295 | 0.257 | 0.255 |
| 5.0 | 1.499 | 1.499 | 0.250 | 0.212 | 0.210 |
| 10.0 | 1.658 | 1.658 | 0.409 | 0.371 | 0.369 |

| (B) Etopside (µM) | | | | | |
|---|---|---|---|---|---|
| LtxA (µg/ml) | 0.017 | 0.169 | 1.699 | 16.99 | 84.953 |
| 0.01 | *0.997* | 0.728 | 0.110 | 0.089 | 0.102 |
| 0.1 | *0.961* | 0.692 | 0.074 | 0.052 | 0.066 |
| 1.0 | *0.953* | 0.684 | 0.066 | 0.045 | 0.058 |
| 5.0 | *0.946* | 0.676 | 0.059 | 0.037 | 0.051 |
| 10.0 | *0.959* | 0.689 | 0.072 | 0.050 | 0.064 |

| (C) Etopside (µM) | | | | | |
|---|---|---|---|---|---|
| LtxA (µg/ml) | 0.17 | 1.7 | 16.99 | 84.95 | 169.91 |
| 0.1 | *1.051* | *1.051* | 0.054 | 0.042 | 0.054 |
| 1.0 | *1.023* | *1.023* | 0.026 | 0.009 | 0.026 |
| 5.0 | *1.060* | *1.060* | 0.063 | 0.011 | 0.063 |
| 10.0 | *1.056* | *1.056* | 0.059 | 0.043 | 0.059 |
| 30.0 | *1.089* | *1.089* | 0.092 | 0.005 | 0.092 |

Combination index values for LtxA and etoposide against: (A)—THP-1 cells; (B)—GDM-1 cells; and (C)—HL-60 cells; Bolded font reflects values in the synergistic range; Italicized font represent values in the additive range and Plain font represent values in the antagonistic range.

Mitoxantrone. THP-1, GDM-1, and HL-60 cells were tested with mitoxantrone (Cmax=650 nM, (Nicoletto M O, et al. Cancer Chemother Pharmacol. 2000; 45:457-462)). For THP-1 cells, synergy was observed at 1.0 µg/ml LtxA and doses of mitoxantrone in the range of its Cmax. Increasing concentrations of LtxA resulted in very strong synergy. For GDM-1 cells, very strong synergy was observed at the lowest dose of LtxA (0.01 µg/ml). Interestingly, as the LtxA concentration increased, the synergy potential decreased. For HL-60 cells, strong synergy was seen for 0.1 µg/ml LtxA and very strong synergy at the highest doses of LtxA (10 µg/ml).

| (A) Mitoxantrone (nM) | | | | | |
|---|---|---|---|---|---|
| LtxA (µg/ml) | 0.19 | 1.93 | 19.33 | 193.27 | 1932.7 |
| 0.01 | 14.323 | 14.323 | 13.061 | 13.040 | 13.034 |
| 0.1 | 2.113 | 2.113 | 0.852 | 0.830 | 0.824 |
| 1.0 | 1.492 | 1.492 | 0.231 | 0.210 | 0.203 |
| 5.0 | 1.314 | 1.314 | 0.053 | 0.032 | 0.025 |
| 10.0 | 1.323 | 1.323 | 0.062 | 0.041 | 0.034 |

| (B) Mitoxantrone (nM) | | | | | |
|---|---|---|---|---|---|
| LtxA (µg/ml) | 0.19 | 1.93 | 19.33 | 193.27 | 1932.7 |
| 0.01 | *0.991* | *0.991* | 0.059 | 0.053 | 0.049 |
| 0.1 | *1.058* | *1.058* | 0.125 | 0.119 | 0.115 |
| 1.0 | 1.165 | 1.165 | 0.232 | 0.226 | 0.222 |
| 5.0 | 1.355 | 1.355 | 0.422 | 0.417 | 0.413 |
| 10.0 | 1.547 | 1.547 | 0.614 | 0.608 | 0.604 |

| (C) Mitoxantrone (nM) | | | | | |
|---|---|---|---|---|---|
| LtxA (µg/ml) | 0.19 | 1.93 | 19.33 | 193.27 | 1932.7 |
| 0.1 | 1.223 | 0.546 | 0.237 | 0.226 | 0.226 |
| 1.0 | 1.230 | 0.554 | 0.244 | 0.244 | 0.244 |
| 5.0 | 1.143 | 0.467 | 0.157 | 0.157 | 0.157 |
| 10.0 | *1.002* | 0.326 | 0.016 | 0.016 | 0.016 |
| 30.0 | *1.004* | 0.327 | 0.018 | 0.018 | 0.018 |

Combination index values for LtxA and mitoxantrone against: (A)—THP-1 cells; (B)—GDM-1 cells; and (C)—HL-60 cells; Bolded font reflects values in the synergistic range; Italicized font represent values in the additive range and Plain font represent values in the antagonistic range.

Daunorubicin. THP-1, GDM-1, and HL-60 cells were tested with daunorubicin (Cmax=200 nM (Sun Y N, et al.

Zhonghua er ke za zhi. 2009; 47:296-300). For THP-1 cells, strong synergy was observed at 0.01 μg/ml LtxA and doses of daunorubicin in the range of its Cmax. At higher doses of LtxA, very strong synergy was detected. For GDM-1 cells, very strong synergy was seen at 0.01 μg/ml LtxA. HL-60 cells revealed antagonism under all the conditions tested.

| (A) Daunorubicin (nM) | | | | | |
|---|---|---|---|---|---|
| LtxA (μg/ml) | 1.77 | 17.73 | 177.31 | 1773.08 | 17730.8 |
| 0.01 | 0.630 | 0.109 | 0.105 | 0.105 | 0.105 |
| 0.1 | 0.638 | 0.116 | 0.113 | 0.113 | 0.113 |
| 1.0 | 0.534 | 0.012 | 0.009 | 0.009 | 0.009 |
| 5.0 | 0.550 | 0.028 | 0.025 | 0.025 | 0.025 |
| 10.0 | 0.530 | 0.009 | 0.005 | 0.005 | 0.005 |

| (B) Daunorubicin (nM) | | | | | |
|---|---|---|---|---|---|
| LtxA (μg/ml) | 0.18 | 1.77 | 17.73 | 177.31 | 1773.08 |
| 0.01 | *0.990* | *0.990* | 0.048 | 0.048 | 0.048 |
| 0.1 | *0.972* | *0.972* | 0.030 | 0.030 | 0.030 |
| 1.0 | *0.967* | *0.967* | 0.024 | 0.024 | 0.024 |
| 5.0 | *0.950* | *0.950* | 0.008 | 0.008 | 0.008 |
| 10.0 | *0.961* | *0.961* | 0.019 | 0.019 | 0.019 |

| (C) Daunorubicin (nM) | | | | | |
|---|---|---|---|---|---|
| LtxA (μg/ml) | 1.77 | 17.73 | 177.31 | 1773.08 | 17730.8 |
| 0.1 | 3.564 | 3.564 | 2.567 | 2.567 | 2.567 |
| 1.0 | 3.161 | 3.161 | 3.161 | 3.161 | 3.161 |
| 5.0 | 2.877 | 2.877 | 2.877 | 2.877 | 2.877 |
| 10.0 | 2.436 | 2.436 | 2.436 | 2.436 | 2.436 |
| 30.0 | 3.555 | 3.555 | 3.555 | 3.555 | 3.555 |

Combination index values for LtxA and daunorubicin against: (A)—THP-1 cells; (B)—GDM-1 cells; and (C)—HL-60 cells; Bolded font reflects values in the synergistic range; Italicized font represent values in the additive range and Plain font represent values in the antagonistic range.

Busulfan. Combinations of LtxA and busulfan were tested (Cmax=4.7 μM (Schechter T, et al. Biol Blood Marrow Transplant. 2007; 13:307-314)) against the CML cell line, KU-812 (FIG. 5A). Strong synergy was observed at an LtxA dose of 0.0001 μg/ml and concentration of busulfan in the range of its Cmax. At doses of 0.001 μg/ml LtxA and higher, very strong synergy was detected.

| A) Busulfan (μM) | | | | | |
|---|---|---|---|---|---|
| LtxA (μg/ml) | 0.41 | 4.06 | 40.6 | 203 | 406 |
| 0.00001 | 0.869 | 0.825 | 0.808 | 0.772 | 0.772 |
| 0.0001 | 0.153 | 0.109 | 0.092 | 0.056 | 0.056 |
| 0.001 | 0.111 | 0.067 | 0.050 | 0.014 | 0.014 |
| 0.01 | 0.140 | 0.096 | 0.079 | 0.043 | 0.043 |
| 0.1 | 0.112 | 0.068 | 0.051 | 0.015 | 0.015 |

Combination index values for LtxA and busulfan against: KU-812 CML cells; Bolded font reflects values in the synergistic range; Italicized font represent values in the additive range and Plain font represent values in the antagonistic range.

Imatinib. Imatinib (Cmax=6650 nM (Wang Y, et al. British journal of clinical pharmacology. 2008; 65:885-892)) and LtxA were tested against KU-812 cells. At the lowest dose of LtxA (0.00001 μg/ml), antagonism was observed at all concentrations of imatinib. However at 0.0001 μg/ml and higher, very strong synergy was observed when the dose of imatinib was greater than 169 nM.

| B) Imatinib (nM) | | | | | |
|---|---|---|---|---|---|
| LtxA (μg/ml) | 0.17 | 1.69 | 16.96 | 1.69.58 | 1695.78 |
| 0.00001 | >3.0 | >3.0 | >3.0 | >3.0 | >3.0 |
| 0.0001 | *1.098* | >3.0 | 0.852 | 0.091 | 0.074 |
| 0.001 | *1.085* | >3.0 | 0.839 | 0.078 | 0.060 |
| 0.01 | 1.125 | >3.0 | 0.879 | 0.118 | 0.100 |
| 0.1 | *1.047* | >3.0 | 0.801 | 0.039 | 0.022 |

Combination index values for LtxA and imatinib against: KU-812 CML cells; Bolded font reflects values in the synergistic range; Italicized font represent values in the additive range and Plain font represent values in the antagonistic range.

Primary cells from different diseases are sensitive to LtxA. The specificity for LFA-1 and mechanism of LtxA-mediated cytotoxicity may suggest broad use of LtxA for treatment of different types of hematological malignancies. It was found that primary cells from AML, acute lymphocytic leukemia (ALL), mantle cell lymphoma (MCL), diffuse large B-cell lymphoma (DLBL), and follicular lymphoma (FLL) patients were all highly sensitive to LtxA as a single agent. Of significance, even cells that were isolated from relapsed or refractory patients exhibited high susceptibility to LtxA.

For all the standard drugs tested, synergy was observed at concentrations well below their tolerated $C_{max}$ values. Administration of the LtxA to rodents and non-human primates was very well-tolerated (Kachlany S C, et al. 2010; 34:777-785). The dose administered to rodents has been in the range of 1.0 mg/kg, which is equivalent to ~10 μg LtxA/ml blood. In the non-human primate, the injected dose of 22 μg/kg is equivalent to ~0.4 μg LtxA/ml blood. The LtxA/daunorubicin combination, the ratio between the effective concentration of LtxA in vitro and the tolerated concentration in vivo is ~1:40, it is assumed that 0.4 μg LtxA/ml blood to a be a conservative tolerated dose based on the non-human primate studies.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patent applications and U.S. patents cited in this disclosure are incorporated herein by reference in their entireties. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A pharmaceutical composition comprising an effective amount of leukotoxin, an effective amount of at least one other chemotherapeutic agent, and a pharmaceutically acceptable carrier, wherein the effective amounts are selected such that they synergistically induce apoptosis of a cancer cell, and wherein the other chemotherapeutic agent is selected from the group consisting of busulfan, imatinib and imatinib mesylate.

2. The composition of claim 1, wherein the other chemotherapeutic agent is imatinib or imatinib mesylate.

3. The composition of claim 1, wherein the other chemotherapeutic agent is busulfan.

4. The composition of claim 1, wherein the cancer cell is a hematological cancer cell.

5. The composition of claim 4, wherein the hematological cancer cell is selected from the group consisting of a leukemia cell, a lymphoma cell, and a myeloma cell.

6. A kit comprising a pharmaceutically acceptable dose unit of a pharmaceutically effective amount of leukotoxin, and a pharmaceutically acceptable dose unit of a pharmaceutically effective amount of a chemotherapeutic agent selected from the group consisting of bisulfan, imatinib and imatinib mesylate, wherein the two pharmaceutically acceptable dose units can optionally take the form of a single pharmaceutically acceptable dose unit, and wherein the pharmaceutically effective amounts are selected such that they synergistically induce apoptosis of a cancer cell.

7. The kit of claim 6, wherein the other chemotherapeutic agent is imatinib or imatinib mesylate.

8. The kit of claim 6, wherein the other chemotherapeutic agent is busulfan.

9. The kit of claim 1, wherein the cancer cell is a hematological cancer cell.

10. The kit of claim 9, wherein the hematological cancer cell is selected from the group consisting of a leukemia cell, a lymphoma cell, and a myeloma cell.

11. A method for inducing apoptosis of a cancer cell expressing leukocyte function antigen (LFA-1), comprising contacting the cell with the pharmaceutical composition of claim 1.

12. The method of claim 11 wherein the other chemotherapeuric agent is busulfan.

13. The method of claim 11 wherein the other chemotherapeutic agent is imatinib or imatinib mesylate.

14. The method of claim 11 wherein the leukotoxin and the other chemotherapeutic agent are contacted with the cell simultaneously or sequentially.

15. The method of claim 11 wherein the cancer cell is a hematological cancer cell.

16. The method of claim 15 wherein the hematological cancer cell is selected from the group consisting of a leukemia cell, a lymphoma cell, and a myeloma cell.

17. A method for treating a hematological cancer in a subject in need of such treatment comprising administering an effective amount of the pharmaceutical composition of claim 1 to said subject.

18. The method of claim 17 wherein the other chemotherapeutic agent is busulfan.

19. The method of claim 17 wherein the other chemotherapeutic agent is imatinib or imatinib mesylate.

20. The method of claim 17 wherein the leukotoxin and the other chemotherapeutic agent are administered to the subject simultaneously or sequentially.

21. The method of claim 17 wherein the hematological cancer is selected from the group consisting of leukemia, lymphoma, and myeloma.

* * * * *